US010512394B2

United States Patent
Gov-Ari et al.

(10) Patent No.: US 10,512,394 B2
(45) Date of Patent: Dec. 24, 2019

(54) ENDOSCOPIC-ENABLED MOUTH GAG AND ASSOCIATED METHOD OF USE

(71) Applicant: The Curators of the University of Missouri, Columbia, MO (US)

(72) Inventors: Eliav Gov-Ari, Columbia, MO (US); Alexander Madinger, Chesterfield, MO (US)

(73) Assignee: The Curators of the University of Missouri, Columbia, MO (US)

( * ) Notice: Subject to any disclaimer, the term of this patent is extended or adjusted under 35 U.S.C. 154(b) by 363 days.

(21) Appl. No.: 15/025,200

(22) PCT Filed: Sep. 26, 2014

(86) PCT No.: PCT/US2014/057768
§ 371 (c)(1),
(2) Date: Mar. 25, 2016

(87) PCT Pub. No.: WO2015/048481
PCT Pub. Date: Apr. 2, 2015

(65) Prior Publication Data
US 2016/0235287 A1    Aug. 18, 2016

Related U.S. Application Data

(60) Provisional application No. 61/960,786, filed on Sep. 26, 2013.

(51) Int. Cl.
*A61B 1/24* (2006.01)
*A61B 13/00* (2006.01)
(Continued)

(52) U.S. Cl.
CPC .................. *A61B 1/24* (2013.01); *A61B 1/32* (2013.01); *A61B 13/00* (2013.01); *A61B 17/24* (2013.01); *A61B 90/14* (2016.02)

(58) Field of Classification Search
CPC ... A61C 5/007; A61M 16/04; A61M 16/0434; A61M 16/0495; A61B 1/24; A61B 1/32;
(Continued)

(56) References Cited

U.S. PATENT DOCUMENTS 2,969,059 A    1/1961 Meek et al.
4,112,936 A    9/1978 Blachly
(Continued)

FOREIGN PATENT DOCUMENTS

| CN | 101836879 A | 9/2010 |
|---|---|---|
| DE | 102010026552 A1 | 1/2012 |
| EP | 2679145 A1 | 1/2014 |

OTHER PUBLICATIONS

"375116—McIvor Mouth Gags", Global Surgical Instruments, 1 page, retrieved from the Internet on Sep. 30, 2015, <http://www.globalsurgicalinstruments.com/375116>.
(Continued)

*Primary Examiner* — Andrew Yang
(74) *Attorney, Agent, or Firm* — Thompson Coburn LLP; Kevin M. Kercher

(57) ABSTRACT

The present invention discloses a new and improved endoscopic-enabled mouth gag for routine ENT procedures, such as adenoidectomy and nasopharyngeal biopsy. The invention modifies the existing mouth gag, provides a stable and adjustable placement for an endoscopic device potentially employed during an ENT procedure, and is to replace the outdated surgical method where the surgical field is visualized indirectly via a handheld mirror (with or without the preexisting mouth gag). The inventive endoscopic-enabled mouth gag not only provides enhanced visualization of the surgical field for a clinician, assistants, and trainees, but also enables a clinician to perform the procedure bimanually (with both hands).

7 Claims, 11 Drawing Sheets

(51) Int. Cl.
*A61B 1/32* (2006.01)
*A61B 17/24* (2006.01)
*A61B 90/14* (2016.01)

(58) Field of Classification Search
CPC ..... A61B 1/00149; A61B 13/00; A61B 17/02; A61B 17/24; A61B 90/50; A61B 19/14
See application file for complete search history.

(56) References Cited

U.S. PATENT DOCUMENTS

| | | | |
|---|---|---|---|
| 4,198,970 A | 4/1980 | Luomanen | |
| 4,213,451 A | 7/1980 | Swenson | |
| 4,270,531 A | 6/1981 | Blachly et al. | |
| 4,306,547 A | 12/1981 | Lowell | |
| 4,425,911 A | 1/1984 | Luomanen et al. | |
| 4,437,458 A | 3/1984 | Upsher | |
| 4,491,435 A | 1/1985 | Meier | |
| 4,495,945 A | 1/1985 | Liegner | |
| 4,825,858 A | 5/1989 | Frankel | |
| 5,038,766 A | 8/1991 | Parker | |
| 5,069,206 A | 12/1991 | Crosbie | |
| 5,174,283 A | 12/1992 | Parker | |
| 5,203,320 A | 4/1993 | Augustine | |
| 5,203,324 A | 4/1993 | Kinkade | |
| 5,261,392 A | 11/1993 | Wu | |
| 5,339,805 A | 8/1994 | Parker | |
| 5,365,940 A | 11/1994 | Teves | |
| 5,443,058 A | 8/1995 | Ough | |
| 5,590,643 A | 1/1997 | Flam | |
| 5,649,540 A | 7/1997 | Alvarez et al. | |
| 5,665,052 A | 9/1997 | Bullard | |
| 5,800,344 A | 9/1998 | Wood, Sr. et al. | |
| 5,840,013 A | 11/1998 | Lee et al. | |
| 5,897,491 A | 4/1999 | Kastenbauer et al. | |
| 6,257,238 B1 | 7/2001 | Meah | |
| 6,293,908 B1 | 9/2001 | Fujikura et al. | |
| 6,655,377 B2 | 12/2003 | Pacey | |
| 6,718,970 B2 | 4/2004 | Sniadach | |
| 6,955,645 B1 | 10/2005 | Zeitels | |
| 6,966,319 B2 | 11/2005 | Fitton | |
| 7,278,420 B2 | 10/2007 | Ganesh et al. | |
| 7,735,489 B2 | 6/2010 | Mikkaichi et al. | |
| 7,887,483 B2 * | 2/2011 | Rosenberg | A61B 90/14 600/223 |
| 7,909,757 B2 | 3/2011 | Herman | |
| 8,202,215 B2 | 6/2012 | Xiao et al. | |
| 8,297,973 B2 | 10/2012 | Hirsch et al. | |
| 2005/0090712 A1 | 4/2005 | Cubb | |
| 2009/0090475 A1 * | 4/2009 | Raniere | E04B 2/7405 160/351 |
| 2010/0256451 A1 | 10/2010 | McGrath et al. | |
| 2011/0032090 A1 * | 2/2011 | Provancher | G06F 3/016 340/407.1 |
| 2011/0118738 A1 * | 5/2011 | Vasta | A61B 17/62 606/56 |
| 2014/0180006 A1 | 6/2014 | Gov-Ari | |

OTHER PUBLICATIONS

"Davis-Crow Mouth Gags: MO 152", CareFusion—V. Mueller Catalog, 2 pages, retrieved from the Internet on Sep. 30, 2015, <https://catalog.carefusion.com/vmuelle/davis-crowe-mouth-gags-mo152.html>.

"Karl Storz Benjamin-Parsons Operating Laryngoscope", Medical Device Store, 2 pages, retrieved from the Internet on Sep. 30, 2015, <http://medicaldevicestor.com/store/t/ent/instruments/p/benjamin-parsons-operating-laryngoscope>.

International Search Report and Written Opinion for PCT/US2015/057768 dated Jan. 6, 2015.

Supplementary European Search Report for EP14847224 dated Apr. 28, 2017.

* cited by examiner

ENDOSCOPIC-ENABLED MOUTH GAG AND ASSOCIATED METHOD OF USE

CROSS REFERENCE TO RELATED APPLICATIONS

This patent application is a 35 U.S.C. § 371 National Phase of International Patent Application No. PCT/US2014/057768, filed Sep. 26, 2014 and incorporated herein by reference in its entirety, which claims priority of provisional U.S. Patent Application Ser. No. 61/960,786, filed Sep. 26, 2013, and entitled "Endoscopic-Enabled Mouth Gag and Associated Method of Use," the entire disclosure of which is expressly incorporated herein by reference.

STATEMENT REGARDING FEDERALLY SPONSORED RESEARCH OR DEVELOPMENT

None.

FIELD OF THE INVENTION

The present invention relates to a medical device for performing examinations and/or treatments in the upper airway. More particularly, the invention relates to an endoscopic-enabled device for opening the mouth, depressing the tongue, maintaining the airway, and providing enhanced direct visualization at the surgical site.

BACKGROUND OF THE INVENTION

A routine ENT procedure, such as adenoidectomy, is performed under indirect, mirror-aided visualization. FIG. 1 illustrates a conventional ENT procedure with mirror-aided visualization of the surgical field. Alternatively, several different types/sizes of mouth gags are currently employed in the routine ENT procedures. The conventional mouth gag, such as the most commonly used Crowe-Davis and McIvor mouth gags, includes a mouth gag frame and an attachable tongue depressor, whereas the tongue depressor comprises a tongue-covering blade and handle piece to attach to the mouth gag frame. FIG. 2 illustrates a Crowe-Davis mouth gag with a frame and a tongue depressor/blade, whereas the tongue depressor/blade further comprises a rigid groove/indentation on the backside for the passage of an intubation tube between the depressor and the tongue. However, no accommodation is made on any conventional tongue depressor/blade for secure placement of an optic device, such as a fiber optic rigid or flexible endoscope. Rather, during contemporary upper airway procedures (such as nasopharyngeal procedures), a handheld mirror is still used by a surgeon, providing poor imaging quality and limited surgical field viewing. As a result, the surgical field, in such cases, is limited and not magnified, which prevents proper visualization of the surgical field by a surgeon, OR nursing staff, technicians, students and residents. In addition, and most importantly, the handheld mirror occupies a surgeon's non-operating hand.

Endoscopic technology has been increasingly sophisticated to provide high-definition visual monitoring during many types of surgical procedures. Several attempts to combine the endoscopic technology and the existing ENT devices, such as a mouth gag, have been developed and studied; however, most of them are rather cumbersome, and/or focused on developing the direct-line-of-sight from a surgeon's eye to the larynx of a patient. For example, an optical design currently used in robotic surgery, da Vinci Robotic Surgery, is illustrated in FIG. 3. However, the illustrated setup has proven to be cumbersome, significantly limits manual accessibility, and requires a lengthy training to operate. Furthermore, the illustrated robotic surgery, as of now, cannot be utilized for nasopharyngeal surgery, since the adenoids are tucked away in the nasopharynx, located in the opposite direction (~180°) from the larynx, and behind the soft palate, a difficult location to access.

Previously, Dr. Gov-Avi, one of the present inventors, has disclosed a device/method in U.S. Patent Application No. 61/796,514 to incorporate endoscopic means with the conventional mouth gag to provide a clinician with an enhanced viewing of the surgical field during a nasopharyngeal or other ENT surgery. '514 device includes a modified tongue blade with an additional groove/indentation to accommodate the placement of an endoscopic means, as illustrated in FIG. 4a and FIG. 4b. However, the support/adjustment of the endoscopic means remains manual. This endoscopic-enabled tongue depressor is shown in U.S. Patent Application Publication No. 2014/0180006, filed as U.S. patent application Ser. No. 14/079,265 on Nov. 13, 2013, and published Jun. 26, 2014, as "Endoscopic-Enabled Tongue Depressor and Associated Method of Use," which is incorporated by reference herein in its entirety.

Therefore, there is a need to provide a new and improved endoscopic-enabled mouth gag with adjustable support of the endoscopic device to provide enhanced visualization of the surgical field and to enable a clinician to utilize both hands during an ENT surgery.

SUMMARY OF THE INVENTION

The present invention provides a new and improved endoscopic-enabled mouth gag, whereas an endoscopic device potentially employed thereof may be securely supported and adjusted during an ENT procedure to provide enhanced visualization of the surgical field and to enable a clinician to perform the procedure bimanually (with both hands). Specifically, the inventive endoscopic-enabled mouth gag comprises three main members: 1) a modified mouth gag frame, 2) an endoscopic support means providing the adjustable support to an endoscopic device, whereas the support means may be removably and/or collapsibly attached to the mouth gag frame, and 3) a tongue blade. Though the existing tongue blade suffices, a modified tongue blade with a blade ring attached to the blade's front side (opposite side of the tongue) is preferred, whereas the distal end of the endoscopic device suspends through the ring, and the movement of the distal end may be confined/controlled with desired degree of freedom by the ring.

More specifically, the modified mouth gag frame, which is modified upon the preexisting Crowe-Davis mouth gag, opens a patient's mouth, and provides a platform for the endoscopic support means. The modified mouth gag frame, having the mouth piece and the handle piece similar as the existing Crowe-Davis, further comprises a supporting bar and a plurality of socket bases (for the removable ball and socket joints) for attaching the endoscopic support means.

The endoscopic support means comprises an adjustable main shaft and a plurality of adjustable supporting shafts, whereas the main and supporting shafts are so positioned to form a stable and adjustable support for the endoscopic device. Each shaft (main or supporting) comprises a set of outer and inner cylinders and is adjustable lengthwise (along the z axis) by a sliding-and-catching mechanism between the outer and inner cylinders. Each shaft (main or supporting) is attached via a removable ball-and-socket joint at its bottom end to the modified gag frame. Each removable joint is equipped with a "snapping" mechanism, so that the ball can be snapped in (assembly process) or snapped out (removal process) of its socket base. Each supporting shaft is attached via a fixed ball-and-socket joint at its top end to the upper section of the main shaft. The endoscopic support means also comprises a ring holder attached to the top end of the main shaft via a fixed ball-and-socket joint, whereas the camera portion of the employed endoscopic device may be placed upon the ring holder. The ball-and-socket joints, removable (attached to the modified gag frame) or fixed (attaching the supporting shaft to the main shaft or the ring holder to the main shaft), allow for fluid multi-axial movement (along the x and y axes) and play a vital role in the function of the endoscopic support means. Each ball-and-socket joint on the main shaft also comprises a lock. Unlocking the lock at the bottom removable joint frees the main and supporting shafts to be adjusted, whereas locking such lock fix the structure when desired position is achieved. Likewise, unlocking the lock at the top fixed joint frees the ring holder to be adjusted, whereas locking such lock fix the ring holder when desired angel is achieved.

The modified tongue blade comprises a blade ring over the rising groove (for intubation) of an existing Crowe-Davis tongue blade, whereas the distal end of the endoscopic device is suspended through the ring. Various sizes or shapes of the ring may be employed to confine the movement of the distal end of the endoscopic device within the desired degree of freedom. Though the inventive endoscopic-enabled mouth gag is described as modified upon the preexisting Crowe-Davis mouth gag, other types of preexisting mouth gag may be modified accordingly.

BRIEF DESCRIPTION OF THE DRAWINGS

For a better understanding of the present invention, reference may be made to the accompanying drawings in which.

Figure 1:
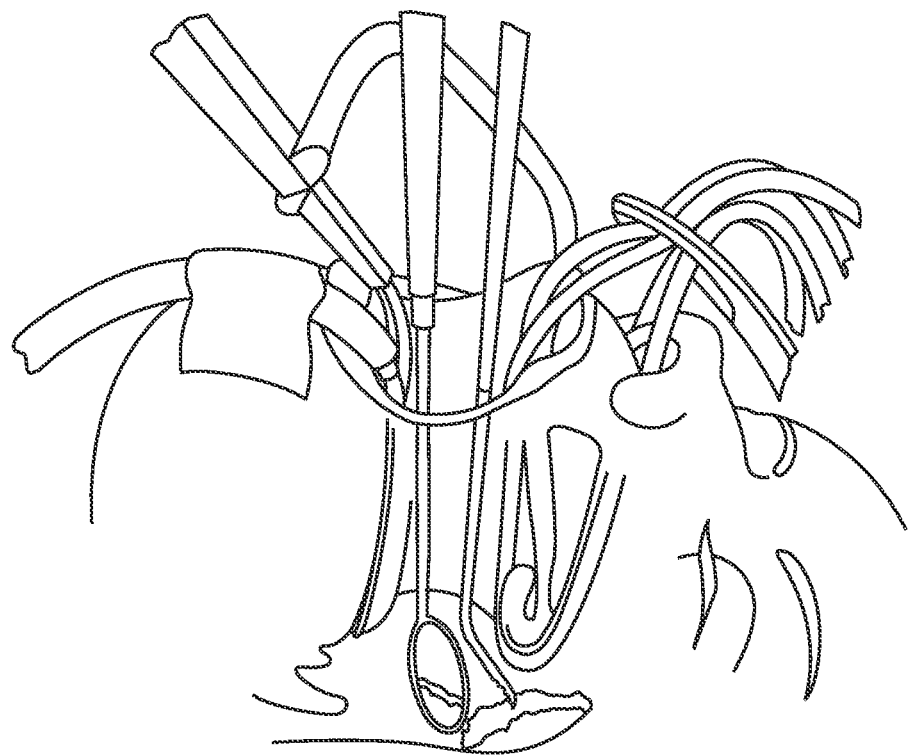
FIG. 1 illustrates a conventional ENT setup under indirect, mirror-aided visualization.
Figure 2:
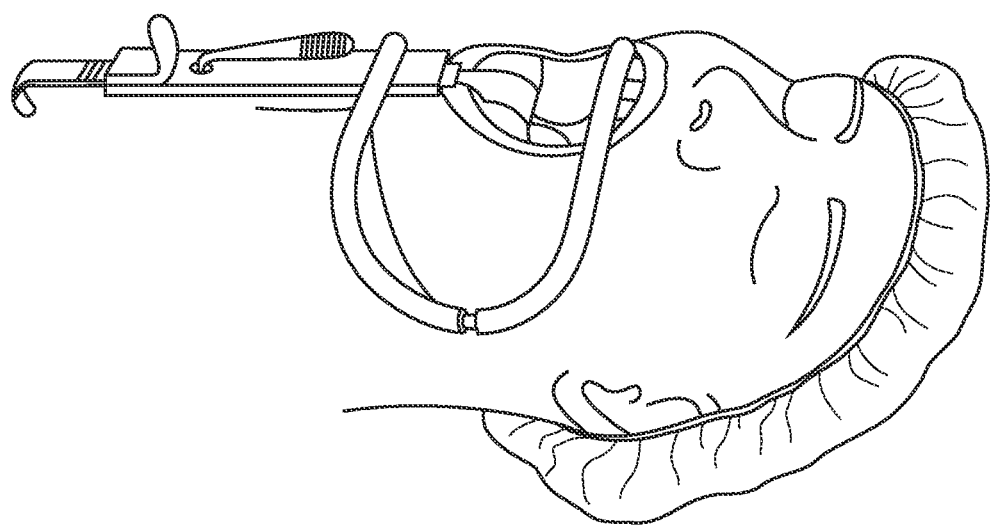
FIG. 2 illustrates an ENT setup with an existing Crowe-Davis mouth gag.
Figure 3:
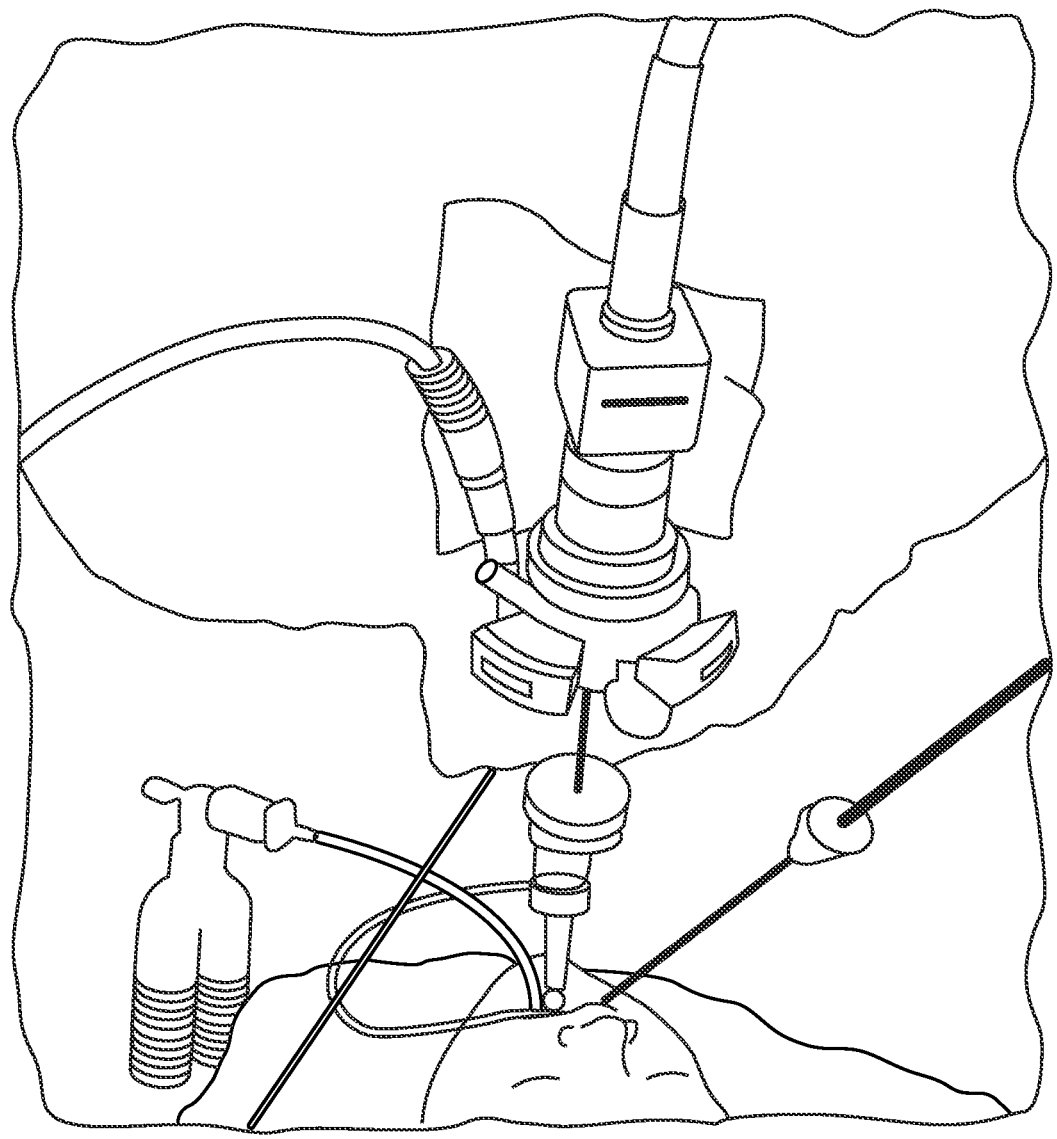
FIG. 3 illustrates the conventional robotic surgery setup.
Figure 4A:
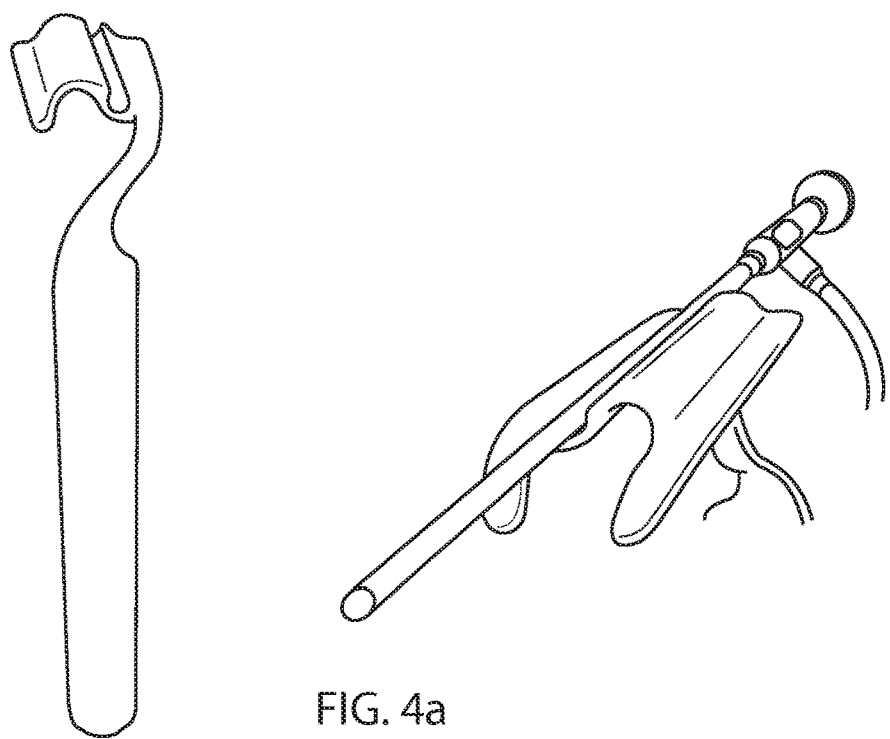
FIG. 4a illustrates an exemplary modified tongue blade according to the inventor's prior invention.
Figure 4B:
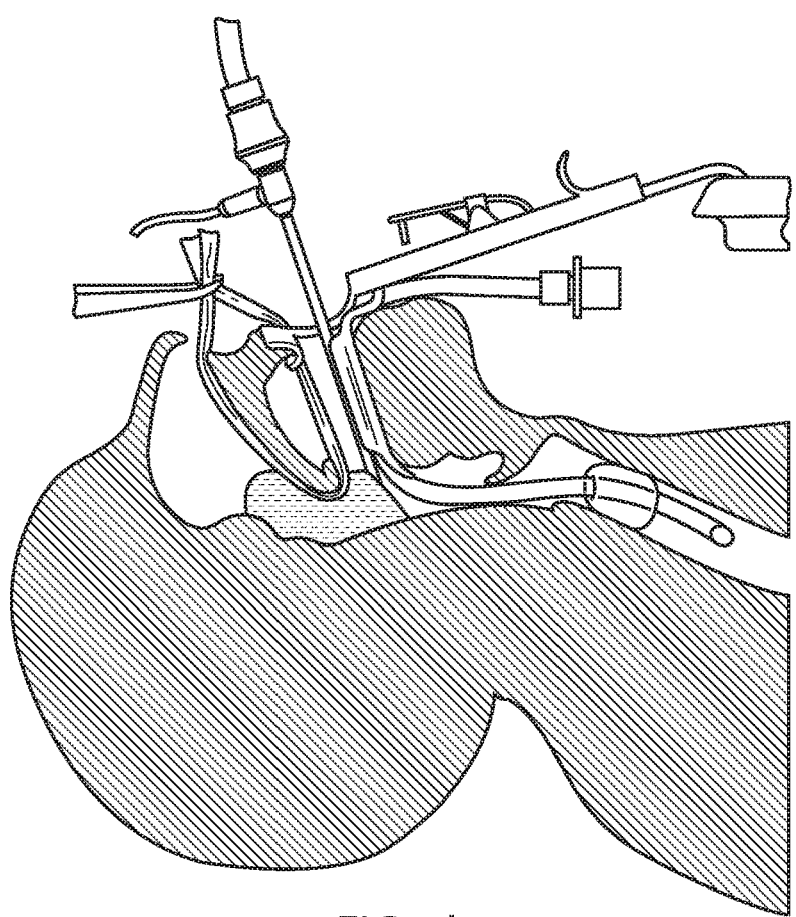
FIG. 4b illustrates an ENT setup employing the modified tongue blade according to the inventor's prior invention.

Reference characters in the written specification indicate corresponding items shown throughout the drawing figures.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to obscure the present invention.

The present invention discloses a new and improved endoscopic-enabled mouth gag for routine ENT procedures, such as adenoidectomy and nasopharyngeal biopsy. The invention modifies the existing mouth gag, provides a stable and adjustable placement for an endoscopic device potentially employed during an ENT procedure, and is to replace the outdated surgical method where the surgical field is visualized indirectly via a handheld mirror (with or without the preexisting mouth gag). The inventive endoscopic-enabled mouth gag not only provides enhanced visualization of the surgical field for clinicians, assistants, and trainees, but also enables a clinician to perform the procedure bimanually (with both hands).

The inventive endoscopic-enabled mouth gag incorporates and modified the existing mouth gag having a mouth gag frame and a tongue depressor/blade with groove for intubation. Though the inventive endoscopic-enabled mouth gag is described as modified upon the preexisting Crowe-Davis mouth gag, other types of preexisting mouth gag may be modified accordingly.

Figure 5:
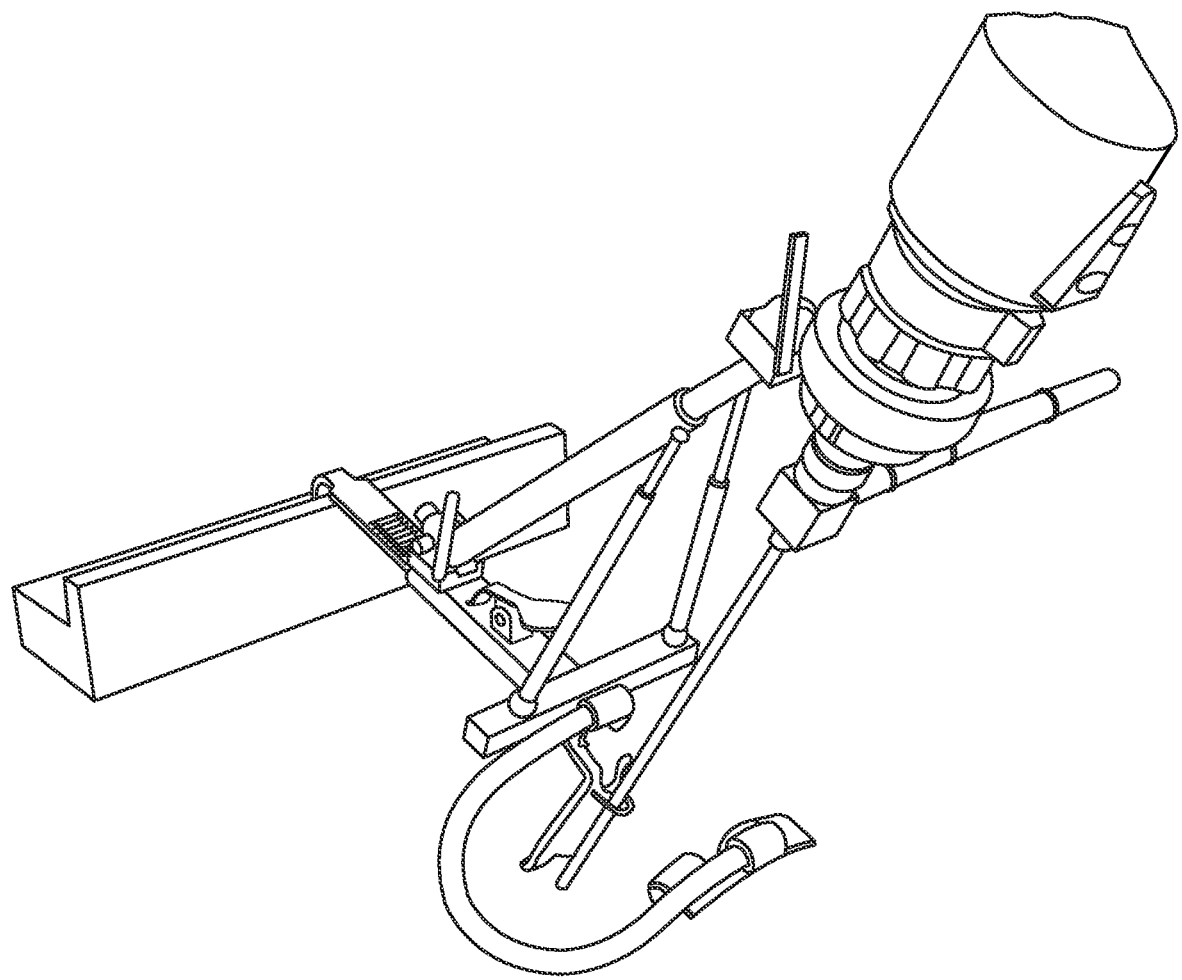
FIG. 5 illustrates an exemplary endoscopic-enabled mouth gag with a potentially employed endoscopic device supported thereby.

The inventive endoscopic-enabled mouth gag comprises three main members: 1) a modified mouth gag frame, 2) an endoscopic support means providing the adjustable support to an endoscopic device, whereas the support means is removably attached to the mouth gag frame, and 3) a tongue blade. The tongue blade may be the existing tongue blade or a modified tongue blade with a ring attached to the blade's rising groove. The modified tongue blade is preferred, since the distal end of the endoscopic device may pass through the ring, and the movement of the distal end may be confined within certain desired degree of freedom by the ring. Refer to FIG. 5, which illustrates an exemplary endoscopic-enabled mouth gag with an endoscopic device supported thereupon.

Figure 6A:
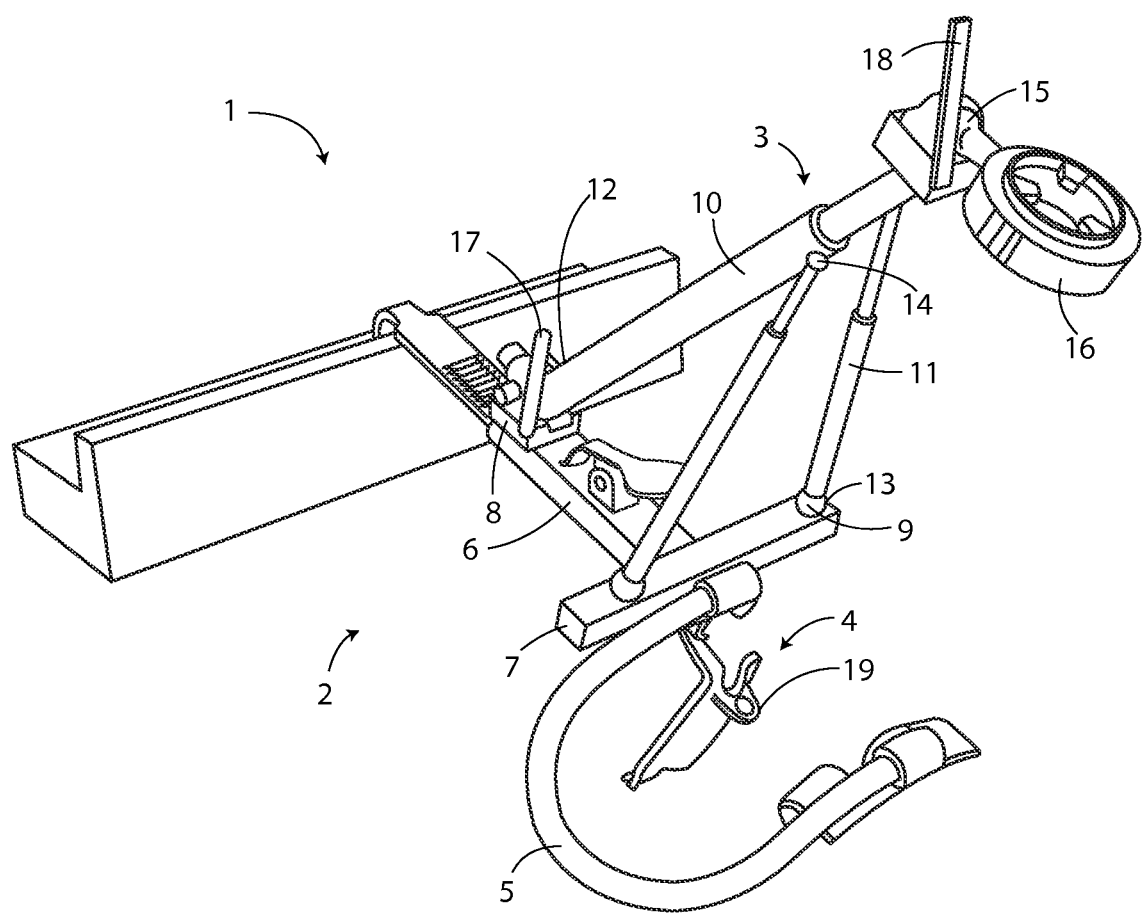
FIGS. 6a and 6b illustrate a set of alternative embodiment of the inventive endoscopic-enabled mouth gag.
Figure 6B:
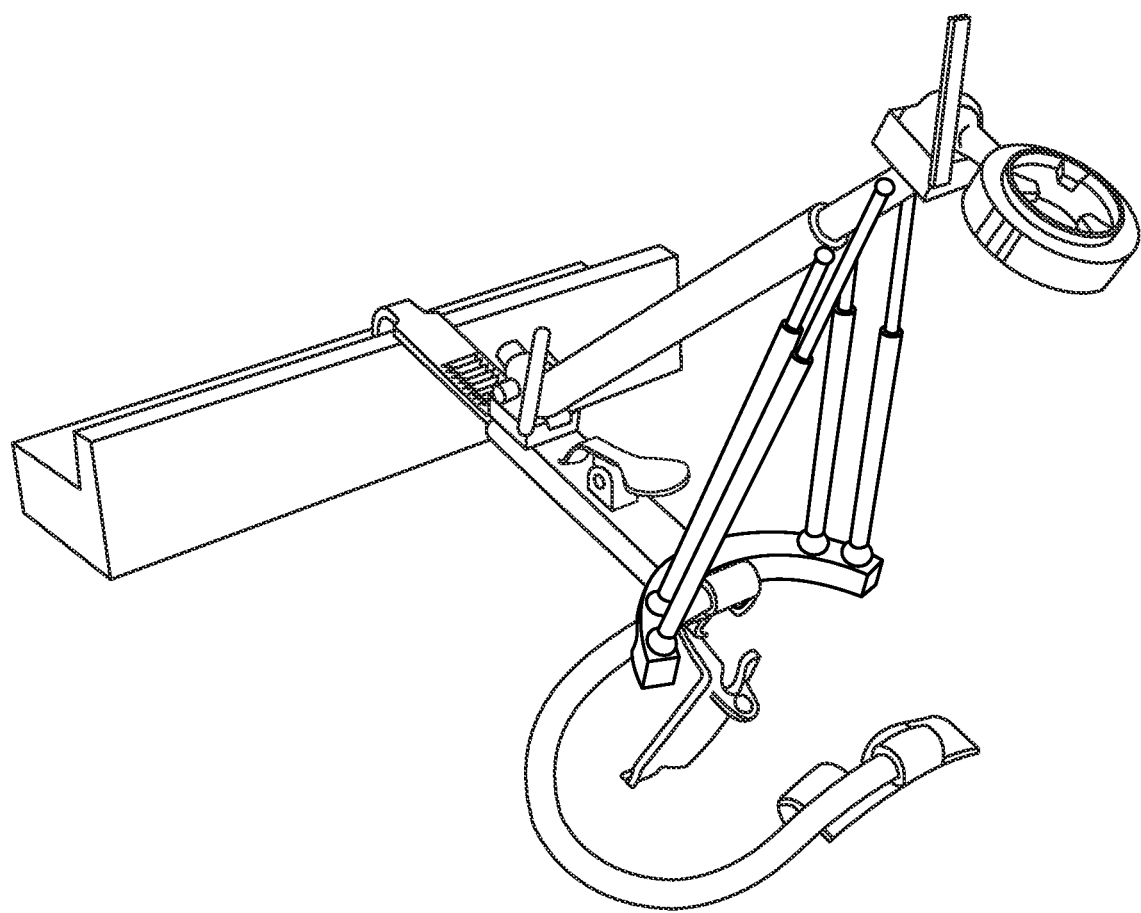

Refer to FIGS. 6a and 6b, which illustrate a set of alternative embodiments of the inventive endoscopic-enabled mouth gag. In FIG. 6a, a three-shaft system is disclosed, whereas a five-shaft system is shown in FIG. 6b. As shown in FIG. 6a, the inventive endoscopic-enabled mouth gag, 1, includes three main members: a modified gag frame, 2, support means, 3, and modified blade, 4. The modified gag frame, 2, includes not only the mouth piece, 5, and handle piece, 6, similar to the existing gag frame, but also a support bar, 7, and a plurality of socket bases, 8 and 9, for the removable attachment of the support means, 3. The support bar, 7, may be straight (as shown in FIG. 6a) or curved (as shown in FIG. 6b) and is located on the handle piece, 6, closely adjacent to the mouth piece, 5. The socket base, 8, for the main shaft (as described below) is fixed on the distal end of the handle piece, 6; the socket bases, 9, for the supporting shaft (as described below) is fixed on the support bar, 7. The relative positions of the socket bases, 8 and 9, is so determined to provide a stable support for the supporting means, 3, and the endoscopic device potentially employed thereof.

Again refer to FIG. 6a. The support means, 3, further includes a main shaft, 10, and a plurality of supporting shafts, 11. A removable ball-and-socket joint, 12, at the bottom end of the main shaft, 10, can be snapped in and out of the socket base, 8, providing a removable attachment of the main shaft, 10, to the handle piece, 6. Similarly, a removable ball-and-socket joint, 13, at the bottom end of each supporting shaft, 11, can be snapped in and out the socket base, 9, providing a removable attachment of the supporting shaft, 11, to the support bar, 7. A fixed ball-and-socket joint, 14, at top end of each supporting shaft, 11, connects the supporting shaft, 11, to the main shaft, 10, at its up position, whereas the connection points are so determined to provide stable support for the endoscopic device potentially employed thereof. A fixed ball-and-socket joint, 15, at the top end of the main shaft, 10, connects to a ring holder, 16, for holding/placement of the endoscopic device. The support means, 3, also provides two locks, 17 and 18, for the removable ball-and-socket joint, 12, and the fixed ball-and-socket joint, 15, respectively.

Still again Refer to FIG. 6a. The modified blade, 4, further includes a blade ring, 19, over the proximal end of the raising groove. The blade ring, 19, is so designed to provide a flexible confinement for the distal end of the endoscopic device potentially employed thereof, whereas the blade ring, 19, confines the distal end of the scope while allowing its movement/adjustment within certain desired degrees (described and illustrated below).

Figure 7A:
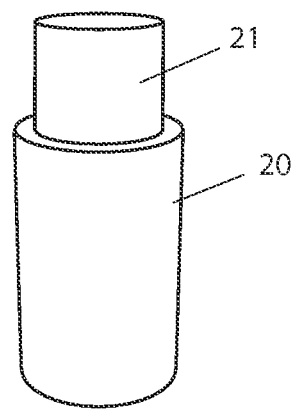
FIGS. 7a and 7b, illustrate the adjustable mechanism of the shaft.
Figure 7B:
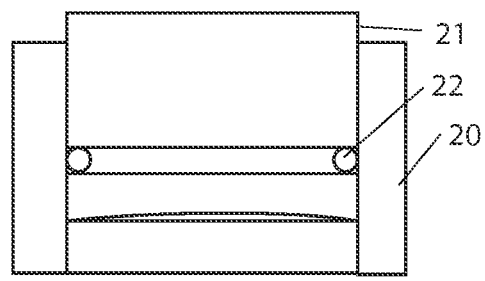

Refer to FIGS. 7a and 7b, which illustrate the adjustable mechanism of the shaft (main and supporting). As shown in FIG. 7a, each shaft is composed of a set of outer and inner cylinders, 20 and 21, respectively, whereas the inner cylinder, 21, is slidingly attached to the outer cylinder, 20. As shown in FIG. 7b, the catching/cutaway means, 22, is installed to stop the sliding when desired length is achieved.

Figure 8A:
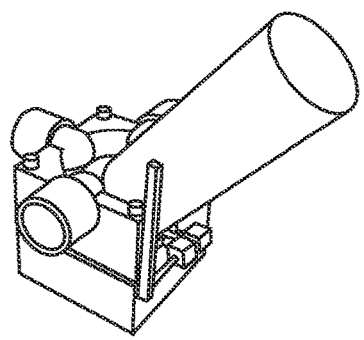
FIGS. 8a to 8c illustrate the detailed assembly of the removable ball-and-socket joint.
Figure 8B:
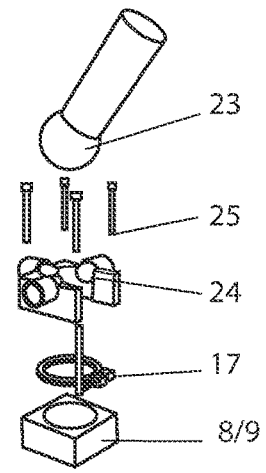
Figure 8C:
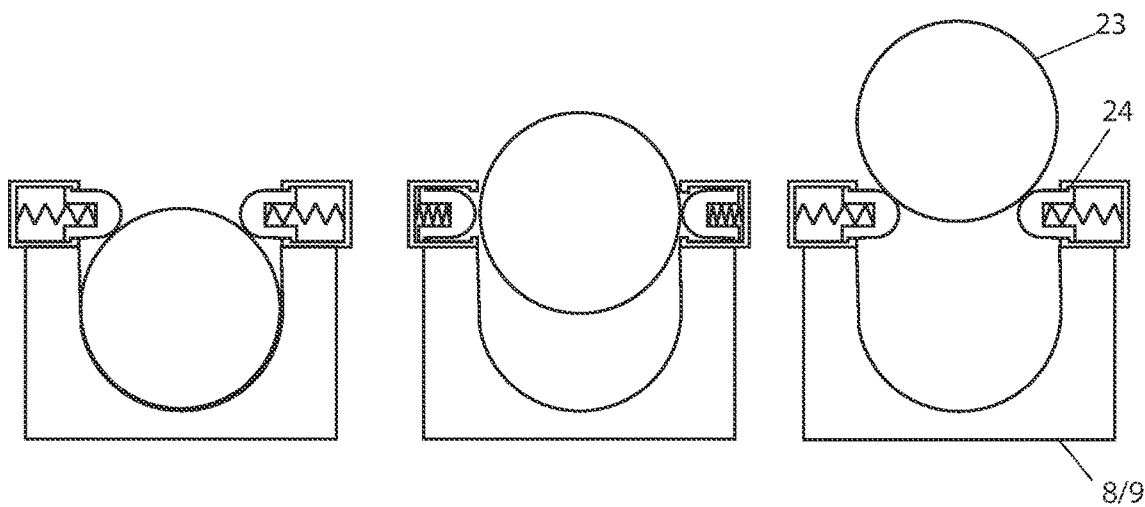

Refer to FIGS. 8a to 8c, which illustrate the detailed assembly of the removable ball-and-socket joint. FIG. 8a is a 3D illustration of an exemplary setup of a joint on the main shaft with the lock, 17. As shown in the exploded view of FIG. 8b, the removable ball-and-socket joint includes a socket base, 8 (9 without lock), fixed on the gag frame, a ball, 23, fixed on the bottom end of a shaft, multiple detents, 24, for retaining and releasing the ball from the socket, and multiple fixing screws, 25, for assembly. FIG. 8c illustrates the snapping mechanism of the removable ball-and-socket joint.

Figure 9A:
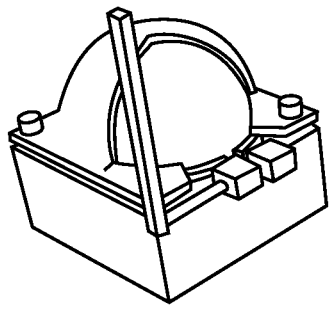
FIGS. 9a and 9b illustrate the detailed assembly of the fixed ball-and-socket joint.
Figure 9B:
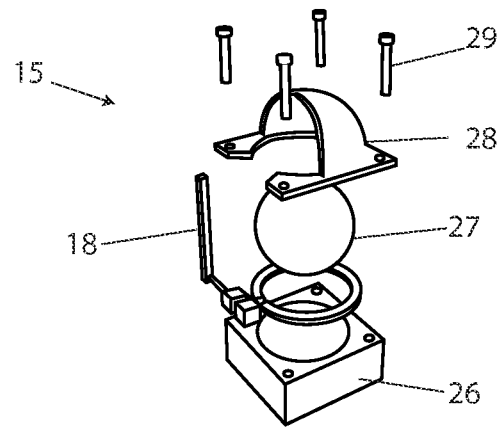

Refer to FIGS. 9a and 9b, which illustrate the detailed assembly of the fixed ball-and-socket joint. As shown in the exploded view, FIG. 9b, the fixed joint, 15 (or 14 without the lock, 18) includes a base socket, 26, which is fixed on the main shaft (at the top end for 15, or on the cylinders for 14), a ball, 27, which is connected to the ring holder, 16 (or the supporting shaft, 11), a joint cap, 28, and multiple fixing screws, 29, for assembly. The joint cap, 28, is partially enclosed to allow the desired rotation of the ball.

Figure 10:
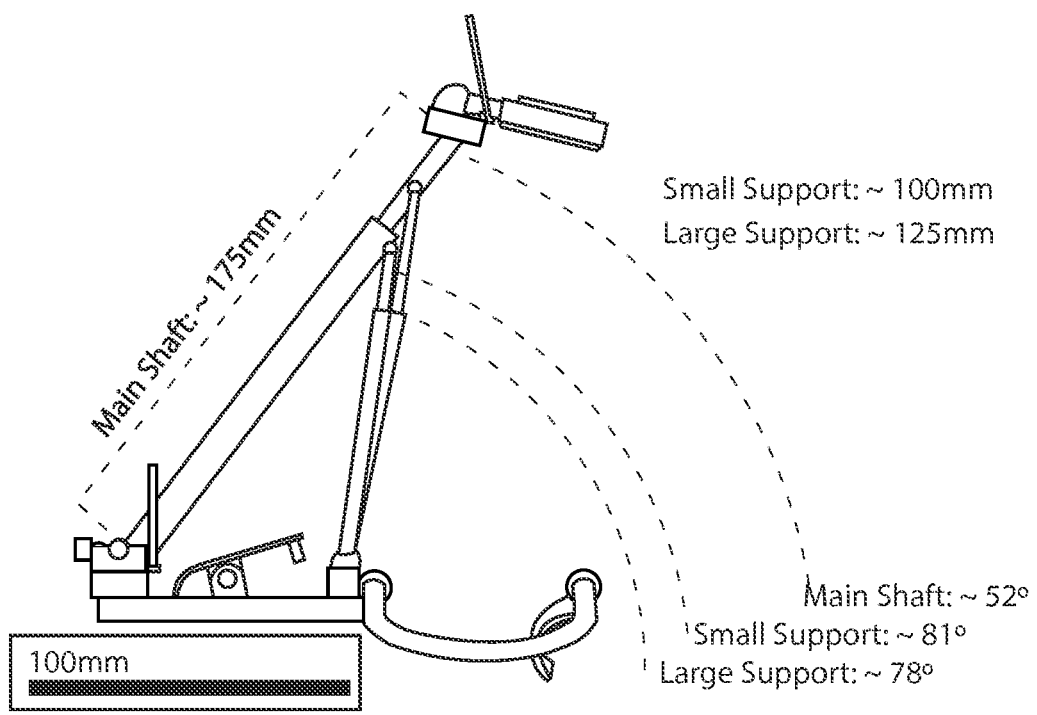
FIG. 10 illustrates an exemplary embodiment of the inventive device with possible measurements of the lengths and angles for a flexible but stable assembly.

The sliding/catching mechanism of the main and supporting shafts provides the vertical (along z axis) adjustment for the supporting system. The ball-and-socket system, removable (attached to the modified gag frame) or fixed (attaching the supporting shaft to the main shaft or the ring holder to the main shaft), allows for fluid multi-axial movement (along the x and y axes). The 3D flexibility of the support means plays a vital role in providing an adjustable support for the endoscopic device potentially employed thereof. Refer to FIG. 10, which illustrates an exemplary embodiment of the inventive device with possible measurements of the lengths and angles for a flexible but stable assembly.

Figure 11:
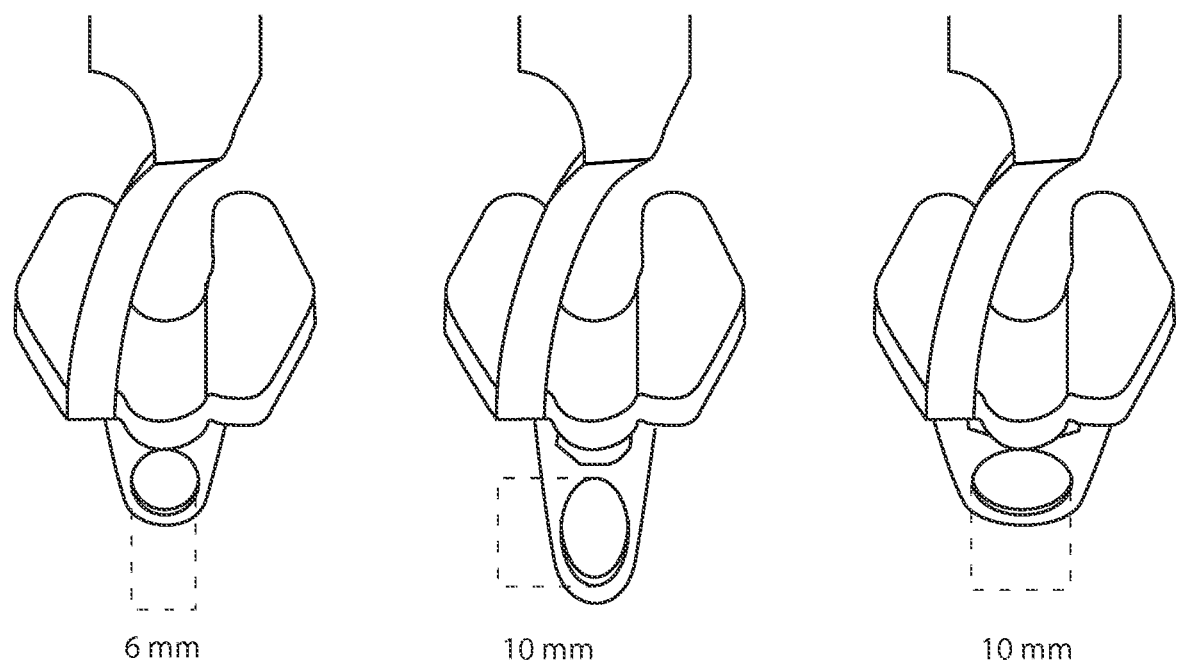
FIG. 11 illustrates three possible designs of the tongue blade ring.

The adjustability of the viewing field of the endoscopic device potentially employed thereof is also confined by the blade ring, 19, on the modified blade, 4. Refer to FIG. 11, which illustrates three possible designs of the tongue blade ring, 19. As shown in FIG. 11, the blade ring, 19, may be round or oval with varying sizes, as long as the blade ring is not limiting the surgical field.

Figure 12A:
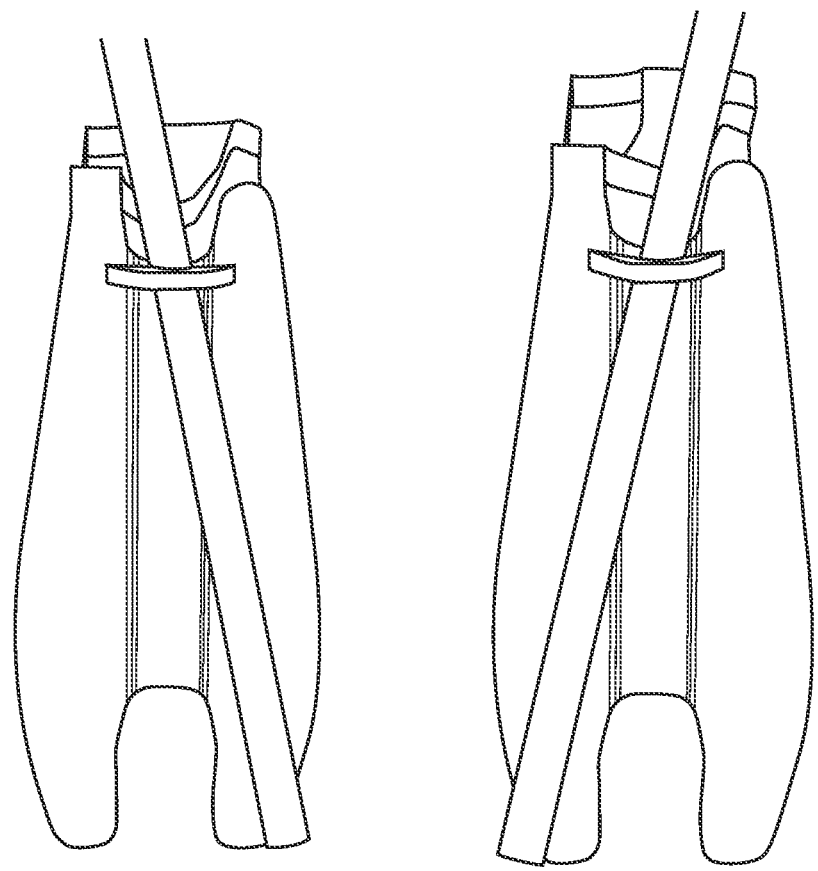
FIGS. 12a to 12c illustrate to ranges of movements of the distal end of an endoscopic device in three axes allowed by the blade ring.
Figure 12B:
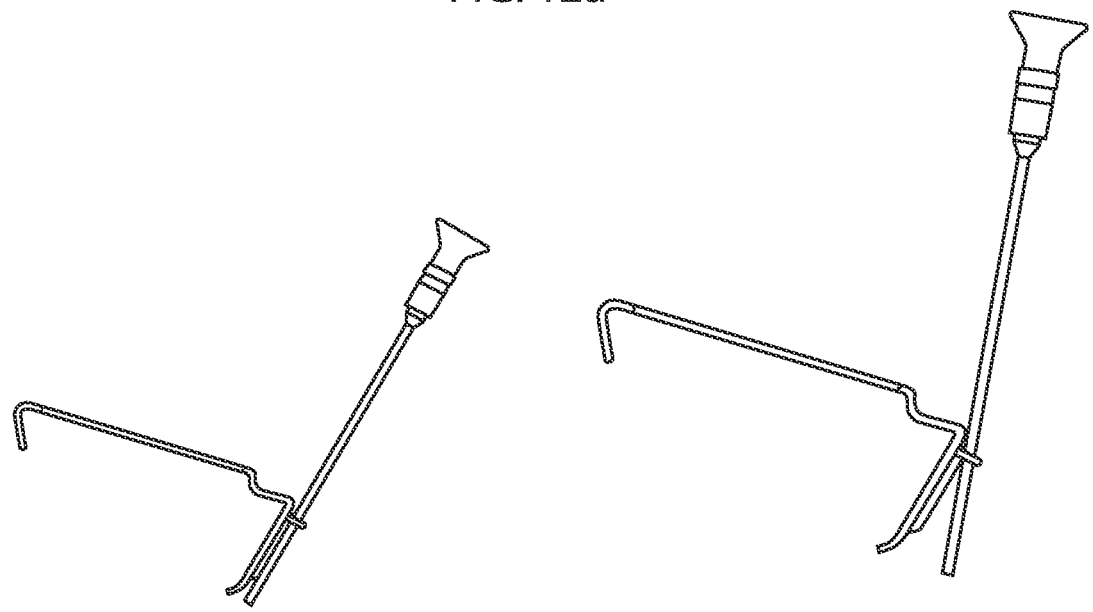
Figure 12C:
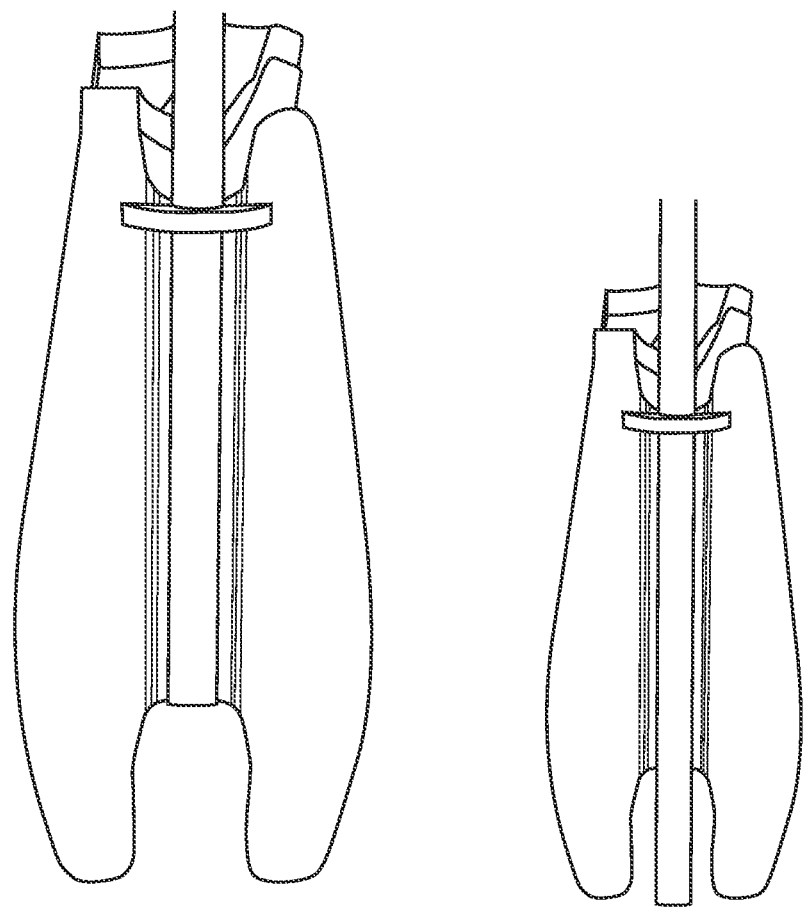

Refer to FIGS. 12a to 12c, which illustrate to ranges of movements of the distal end of an endoscopic device in three axes allowed by the blade ring. FIG. 12a shows the minimum and maximum movements along a first axis; FIG. 12b shows the minimum and maximum movements along a second axis; and FIG. 12c shows the minimum and maximum movements along a third axis.

Figure 13:
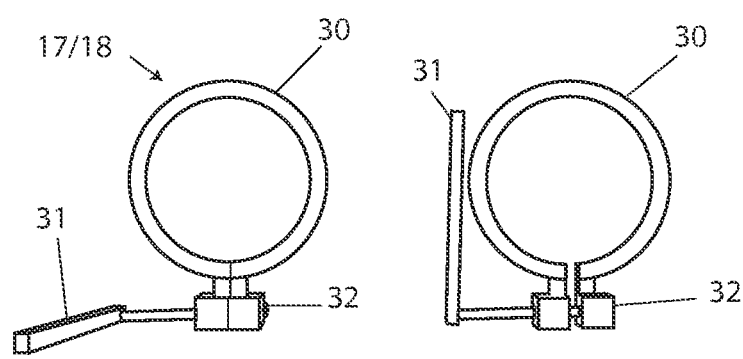
FIG. 13 illustrates the clamp/lever lock employed in one embodiment of the inventive device.

The inventive device further provides two locks on the removable and fixed ball-and-socket joints along the main shaft for the stability and convenience during an ENT procedure. Refer to FIG. 13, which illustrates the clamp/lever lock employed in one embodiment of the inventive device. As shown in FIG. 13, the lock, 17 or 18, includes a clamp ring, 30, a lever, 31, and a screw assembly, 32, whereas the lever may be pushed to clamp or unclamp the ring via the screw assembly.

During an ENT procedure, if a clinician/user wishes to use an endoscopic device, he/she may assemble the support means on to the modified mouth gag frame by simply snapping the balls into the socket bases. Once snapped into place, the user may unlock the joint by freeing a clamp by use of a screw attached to a lever. By pushing this lever to its minimum position, the clamp is undone, allowing the ball to rotate freely within the socket. Once the user has positioned the support means to its desired angle, he/she may reengage the clamp by moving the lever back to its maximum position. After an endoscopic device is inserted through the ring holder with the distal end suspended in the blade ring, the user may further adjust the angle of the endoscopic device by rotating the fixed ball-and-socket joint connecting the ring holder to the main shaft. When the appropriate angle is achieved, the joint connecting the ring holder may also be locked, and the endoscopic device is ready to be used to provide an enhanced visualization of the surgical field. During any point of the procedure, if the user wishes to discard/remove the support means and the endoscopic device suspended thereupon, he/she may simply snap the balls out of the socket bases. As a practical matter, the user will most likely unlock both the main shaft and endoscopic device at the same time by moving the main shaft with one hand and the endoscopic device with the other hand to achieve full 3D motion. Both the main shaft and the endoscopic device will be locked at the same time.

Furthermore, it should be understood that when introducing elements of the present invention in the claims or in the above description of the preferred embodiment of the invention, the terms "have," "having," "includes" and "including" and similar terms as used in the foregoing specification are used in the sense of "optional" or "may include" and not as "required." Similarly, the term "portion" should be construed as meaning some or all of the item or element that it qualifies.

Thus, there have been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

What is claimed is:

1. An endoscopic-enabled mouth gag for an ENT procedure comprising:
   a modified mouth gag frame comprising a support bar and a plurality of socket bases;
   an endoscopic support means removably attached to the modified mouth gag frame, wherein the endoscopic support means adjustably supports the modified mouth gag frame during performance of an ENT procedure; and
   a tongue blade associated with modified mouth gag frame, wherein the endoscopic support means comprises:
      a ring holder for an end of an endoscopic device to be suspended therethrough;
      an adjustable main shaft and a plurality of adjustable supporting shafts, wherein the main and supporting shafts are configured to provide vertical adjustment for the endoscopic support means;
      a plurality of removable ball-and-socket joints on the bottom end of each shaft, attaching each shaft to a respective socket base of the plurality of socket bases of the modified mouth gag frame, wherein the removable ball-and-socket joints are configured to provide multi-axial movement for the shafts and are equipped with a mechanism so that a ball that is associated with a respective shaft of the shafts can be snapped in or snapped out of the respective socket base; and
      a plurality of fixed ball-and-socket joints on the top end of each shaft, wherein the fixed ball-and-socket joints on the supporting shafts connect the top ends of the supporting shafts to the main shaft, wherein the fixed ball-and-socket joints are configured to provide multi-axial movement for the shafts, and the ring holder is connected to the fixed ball-and-socket joint on the main shaft.

2. The endoscopic-enabled mouth gag of claim 1, wherein the main or each supporting shaft further comprises a set of outer and inner cylinders slidingly connected to each other with a cutaway/catching mechanism.

3. The endoscopic-enabled mouth gag of claim 1, wherein the removable ball-and-socket joint on the main shaft further comprises a lock.

4. The endoscopic-enabled mouth gag of claim 1, wherein the fixed ball-and-socket joint on the main shaft further comprises a lock.

5. The endoscopic-enabled mouth gag of claim 1, wherein the tongue blade is an existing tongue blade.

6. The endoscopic-enabled mouth gag of claim 1, wherein the tongue blade is a modified tongue blade comprising a blade ring attached to the blade's front side, and a distal end of the endoscopic device suspends through the blade ring.

7. The endoscopic-enabled mouth gag of claim 6, wherein a hole of the ring holder axially aligns with a hole of the blade ring.

* * * * *